United States Patent
Kanetani et al.

(10) Patent No.: US 8,969,604 B2
(45) Date of Patent: Mar. 3, 2015

(54) SURFACTANT COMPOSITION FOR AGRICULTURAL CHEMICALS

(71) Applicant: Lion Corporation, Tokyo (JP)

(72) Inventors: Akinori Kanetani, Tokyo (JP); Hiroyuki Izumoto, Tokyo (JP); Shiro Sato, Tokyo (JP); Takaaki Kano, Tokyo (JP)

(73) Assignee: Lion Corporation, Tokyo (JP)

( * ) Notice: Subject to any disclaimer, the term of this patent is extended or adjusted under 35 U.S.C. 154(b) by 0 days.

(21) Appl. No.: 13/741,708

(22) Filed: Jan. 15, 2013

(65) Prior Publication Data

US 2013/0131363 A1 May 23, 2013

Related U.S. Application Data

(63) Continuation of application No. 12/948,888, filed on Nov. 18, 2010, which is a continuation of application No. PCT/JP2009/059459, filed on May 22, 2009.

(30) Foreign Application Priority Data

May 23, 2008 (JP) .................................. 2008-135337

(51) Int. Cl.

| | | |
|---|---|---|
| *C07C 67/24* | (2006.01) | |
| *C07C 53/126* | (2006.01) | |
| *C07C 57/03* | (2006.01) | |
| *A01P 7/04* | (2006.01) | |
| *A01N 25/00* | (2006.01) | |
| *C07C 67/08* | (2006.01) | |
| *A01N 25/30* | (2006.01) | |

(52) U.S. Cl.
CPC ................ *C07C 67/24* (2013.01); *A01N 25/30* (2013.01); *C07C 67/08* (2013.01)
USPC ........... 554/167; 554/163; 554/227; 554/223; 504/358; 514/785

(58) Field of Classification Search
None
See application file for complete search history.

(56) References Cited

U.S. PATENT DOCUMENTS 6,184,400 B1 * 2/2001 Hama et al. .................... 554/223
2004/0151749 A1 8/2004 Hasebe et al.

FOREIGN PATENT DOCUMENTS

| CN | 1754429 | | 4/2006 | |
|---|---|---|---|---|
| EP | 0 031 310 | | 7/1981 | |
| JP | 06-329503 | | 11/1994 | |
| JP | 08-157819 | | 6/1996 | |
| JP | 1996-169860 | * | 7/1996 | ............. C07C 69/22 |
| JP | 11-071328 | | 3/1999 | |
| JP | 2959949 | | 10/1999 | |
| JP | 2000-144179 | * | 5/2000 | ............. C11D 1/83 |
| JP | 2001-288006 | | 10/2001 | |
| JP | 2008-031118 A | * | 2/2008 | ............. A61K 8/90 |
| WO | 94/22301 | | 10/1994 | |

OTHER PUBLICATIONS

Machine translation of JP1996-329503.*
Machine translation of JP2000-144179.*
Machine translation of JP1996-329503, 1996.*
Machine translation of JP2000-144179, 2000.*

* cited by examiner

*Primary Examiner* — Mina Haghighatian
*Assistant Examiner* — Erin Hirt
(74) *Attorney, Agent, or Firm* — Carmody Torrance Sandak & Hennessey LLP

(57) ABSTRACT

A surfactant composition for agricultural chemicals, containing fatty acid polyoxyalkylene alkyl ether expressed by the following general formula (I), $$R^1CO(EO)_m(PO)_nOR^2 \qquad (I)$$

wherein the fatty acid polyoxyalkylene alkyl ether has a narrow ratio of 55% by mass or more, where the narrow ratio is expressed by the following formula (A):

Narrow ratio=$\sum_{i=n_{MAX}-2}^{i=n_{MAX}+2} Y_i$ (A).

1 Claim, No Drawings

SURFACTANT COMPOSITION FOR AGRICULTURAL CHEMICALS

CROSS-REFERENCE TO RELATED APPLICATIONS

This is a continuation application of PCT/JP2009/059459, filed on May 22, 2009.

BACKGROUND OF THE INVENTION

1. Field of the Invention

The present invention relates to a surfactant composition for agricultural chemicals, which is suitably used as an emulsifier, dispersing agent, spreading agent, functional spreading agent (adjuvant), and water dispersible agent for agricultural chemicals.

2. Description of the Related Art

In order to allow agricultural chemicals to sufficiently exhibit their effects, formulations of agricultural chemicals, such as bactericides, insecticides, acaricides, weed-killers, and plant growth regulators, are suitably selected considering efficiency for spraying an agricultural chemical for use, safety thereof, or the like. Among such formulations, an emulsified dispersion liquid of an agricultural chemical is expected to be entirely and uniformly deposit on the target for spraying, and has been used in the art. In order to disperse an agricultural chemical, which is generally an oily substance, in water, various surfactants have been used in the emulsified dispersion liquid of the agricultural chemical.

Surfaces of leaves or stems of plants and surfaces of insects have a substance or structure which repels of liquids, or prevents from being wet by liquids. For example, on surfaces of plants, wax-lipoids are secreted, or feathery fibers are closely grown. In another case, fine irregularities are present on surfaces of plants. Moreover, a layer similar to a keratin is present on surfaces of pest insects. All of these materials have such qualities as to repel an aqueous dispersion liquid of agricultural chemicals. Due to this, there are cases where the sprayed agricultural chemical may not provide a sufficient effect thereof. Therefore, spreading agents and functional spreading agents (adjuvants) are used in agricultural chemicals for providing agricultural chemicals with enhanced qualities such as wetting ability, permeability, spreading, and fixing, to thereby increase chemical effects of the agricultural chemicals.

Conventionally, as these surfactants for agricultural chemicals, nonionic surfactants of various alkyl oxide adducts have been known. For example, a spreading agent for agricultural chemicals, which contains a nonionic ester surfactant formed of specific fatty acid polyoxyalkylene alkyl ether, is disclosed in Japanese Patent Application Laid-Open (JP-A) No. 06-329503. An agrochemical spreader composition, which is a surfactant composition excellent in low-temperature stability is disclosed in JP-A No. 2001-288006.

A surfactant for agricultural chemicals formed of a nonionic surfactant is generally used for formulating a fluid agricultural chemical, or is commonly added to a fluid preparation of an agricultural chemical as a fluid spreading agent for an agricultural chemical. Therefore, in actual practices, such surfactant is required to have basic performances such as solubility for dissolving an oil-soluble agricultural chemical component; low foamability and defoamability for improving handling at the time of preformulation in a tank and at the time of spraying, and preventing foaming (polluting) in rivers or the like; and permeability to surfaces of plants and the like, as well as stability which prevents precipitation or separation of substances at the time of use, during storage at low temperature, or when the temperature is changed from low temperature to normal temperature.

BRIEF SUMMARY OF THE INVENTION

The present invention aims at solving various problems in the art, and achieving the following object. Specifically, the object of the present invention is to provide a surfactant composition for agricultural chemicals, which has excellent surface activity (e.g. solubilization ability, dispersibility, permeability, low foamability, and defoaming ability), excellent stability at low temperature, desirable biodegradability, and excellent safety in the environment (e.g. no phytotoxicity and fish toxicity).

Means for solving the aforementioned problems are as follows:

<1> A surfactant composition for agricultural chemicals, containing:

fatty acid polyoxyalkylene alkyl ether expressed by the following general formula (I), wherein the fatty acid polyoxyalkylene alkyl ether has a narrow ratio of 55% by mass or more, where the narrow ratio is expressed by the following formula (A).

$$R^1CO(EO)_m(PO)_nOR^2 \quad (I)$$

In the general formula (I), $R^1CO$ is a C14-22 saturated or unsaturated fatty acid residue; $R^2$ is a C1-3 alkyl group; m and n each express an average number of moles added, where m is an integer of 2 to 10, and n is an integer of 1 to 4; and EO expresses a structural unit of ethylene oxide, and PO expresses a structural unit of propylene oxide, where a form of additions of EO and PO is a block polymer.

$$\text{Narrow ratio} = \Sigma_{i=n_{MAX}-2}^{i=n_{MAX}+2} Y_i \quad (A)$$

In the formula (A), i is the number of moles of alkylene oxide added (the total number of moles of EO and PO which are added), $n_{MAX}$ is the value of i of the fatty acid polyoxyalkylene alkyl ether whose number of moles of alkylene oxide added presents in the largest amount on mass basis among all the fatty acid polyoxyalkylene alkyl ether expressed by the general formula (I), and Yi is a proportion (% by mass) of the fatty acid polyoxyalkylene alkyl ether whose number of moles of alkylene oxide added is i in the entire fatty acid polyoxyalkylene alkyl ether.

<2> A surfactant composition for agricultural chemicals, containing:

the fatty acid polyoxyalkylene alkyl ether as defined in <1>;

water; and

C1-4 lower alcohol, wherein a composition ratio expressed by the fatty acid polyoxyalkylene alkyl ether/the water/the C1-4 lower alcohol is 10% by mass to 60% by mass/10% by mass to 70% by mass/10% by mass to 70% by mass.

According to the present invention, various problems in the art can be solved, the aforementioned object can be achieved, and a surfactant composition for agricultural chemicals, which has an excellent surface activity (solubilization ability, dispersibility, permeability, low foamability, and defoamability), excellent stability at low temperature, and excellent safety in the environment (e.g. no phytotoxicity and fish toxicity) can be provided.

DETAILED DESCRIPTION OF THE INVENTION

The nonionic ester surfactant formed of fatty acid polyoxyalkylene alkyl ether for use in the present invention is fatty acid polyoxyalkylene alkyl ether, which is expressed by the general formula (I) below, and has a narrow ratio of 55% by mass or more, where the narrow ratio is expressed by the formula (A) below.

$$R^1CO(EO)_m(PO)_nOR^2 \quad (I)$$

In the general formula (I), $R^1CO$ is a C14-22 saturated or unsaturated fatty acid residue, $R^2$ is a C1-3 alkyl group, m and n respectively express average numbers of moles of EO and PO added, where m is an integer of 2 to 10, and n is an integer of 1 to 4, EO expresses a structural unit of ethylene oxide, PO expresses a structural unit of propylene oxide, and EO and PO are added in the form of a block polymer.

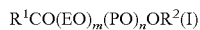

$$\text{Narrow ratio} = \Sigma_{i=n_{MAX}-2}^{i=n_{MAX}+2} Y_i \quad (A)$$

In the formula (A), i is the number of moles of alkylene oxide added (the total number of moles of EO and PO added), $n_{MAX}$ is the value of i of the fatty acid polyoxyalkylene alkyl ether whose number of moles of alkylene oxide added is present in the largest amount on mass basis among all of the fatty acid polyoxyalkylene alkyl ether expressed by the general formula (I), and Yi is a proportion (% by mass) of the fatty acid polyoxyalkylene alkyl ether whose number of moles of alkylene oxide is i in the entire fatty acid polyoxyalkylene alkyl ether.

When the number of carbon atoms in the fatty acid residue $R^1CO$ is 14 to 22, the excellent surface activity such as surface tension, permeability, and low foamability, and excellent safety in the environment such as no phytotoxicity and no fish toxicity are attained. When the number of carbon atoms in $R^1CO$ is in the range of 16 to 18, the surface activity and safety in the environment are improved further.

The fatty acid residue $R^1CO$ can be derived from myristic acid, 5-methyltetradecanoic acid, 2,2-dimethyltetradecanoic acid, pentadecanoic acid, palmitic acid, zoomaric acid (9-hexadecenoic acid), margaric acid, stearic acid, oleic acid, vaccenic acid (11-octadecenoic acid), linoleic acid, linolenic acid, ricinoleic acid (caster oil), 9,10-dihydroxyoctadecanoic acid (caster oil), elaidic acid, isostearic acid, or the like. As seen from the listed examples above, the fatty acid residue $R^1CO$ may have a substituent such as a hydroxyl group.

Also, the fatty acid residue $R^1CO$ may be derived from a mixture of compounds having the substituents, or derived from fatty acid having a composition distribution originated from vegetable oils such as soya bean oil, rape seed oil, and palm oil. Especially, the production quantity of the palm oil is largest among the vegetable oils, and thus there are stable supplies of the palm oil. In addition, the fatty acid derived from the palm oil is preferable, as it has excellent oxidation resistance compared to soya bean oil or rape seed oil.

The fatty acid residue $R^1CO$ is suitably selected depending on the intended purpose without any restriction. For example, in view of low temperature stability, a fatty acid residue having an unsaturated bond, such as oleic acid, linoleic acid, and linolenic acid, is preferable, especially those fatty acid methyl esters, which are in the equivalent form of the fatty acid residue $R^1CO$, having an iodine value of 60 to 150 are preferable, and those having the iodine value of 70 to 130 are more preferable. Moreover, in view of oxidation stability, the iodine value of the fatty acid residue is particularly preferably 70 to 110. Specific examples thereof include M 181 and M182, both manufactured by Lion Corporation, which are fatty acid methyl esters derived from palm oil.

The number of carbon atoms contained in the lower alkyl group $R^2$ is suitably selected depending on the intended purpose without any restriction, but is 1 to 3, preferably 1 to 2, and more preferably 1, i.e. the lower alkyl group being a methyl group, because it can be easily produced.

When the number of carbon atoms in the lower alkyl group $R^2$ is 4 or more, the resulting surfactant composition may have higher fish toxicity and higher phytotoxicity. When the number thereof is 5 or more, in addition to the above, the permeability of the resulting surfactant composition may be decreased. When $R^2$ is a hydrogen atom, the permeability of the resulting surfactant composition may be significantly decreased, and hence the functionality thereof as a spreading agent may be reduced.

The average number "m" of moles of ethylene oxide (EO) that have been added is the range of 2 to 10, preferably 3 to 7. When the average number of moles thereof is smaller than 2, the permeability of the resulting surfactant composition decreases. When the average number of moles thereof is larger than 10, foamability of the resulting surfactant composition is excessively high, as well as having low permeability. In view of desirable permeability and foaming ability of the resulting surfactant composition, the average number of moles of EO that have been added is preferably in the range of 3 to 7.

The average number "n" of moles of propylene oxide (PO) that have been added is in the range of 1 to 4, preferably 2 to 4. When the average number "n" of moles added is 5 or more, the fluid stability of the resulting surfactant composition may be low. When the average number thereof is 0, the permeability of the resulting surfactant composition may be decreased.

The combination of the number of moles of EO added and the number of moles of PO added is preferably such combination that 3 to 7 moles of EO and 2 to 4 moles of PO, because with such combination, the resulting surfactant composition has preferable permeability, low foamability, fluid stability, and safety (without giving any fish toxicity).

The form of addition of EO and PO is a block addition, and the order of the addition needs to be, as presented in the general formula (I), such that PO is added at the terminal (the side of $-OR^2$).

By adding EO and PO in the form of the block addition where PO is added at the terminal, the resulting surfactant composition attains low foamability, excellent permeability, and excellent low temperature stability. Moreover, such surfactant composition has an excellent safety in the environment in view of fish toxicity and the like. On the other hand, when the form of the addition of EO and PO is a random addition, the resulting surfactant composition has poor permeability, and poor stability at low temperature. In addition, those having PO added, not at the terminal, but at the side of the fatty acid residue $R^1CO$, have high foamability, i.e. poor in low foamability.

The fatty acid polyoxyalkylene alkyl ether is suitably selected depending on the intended purpose without any restriction. The fatty acid polyoxyalkylene alkyl ether may be a mixture of alkylene oxide adducts having various numbers of moles of alkylene oxide added. In this case, such fatty acid polyoxyalkylene alkyl ether needs to have a certain distribution of added mole numbers specified by the narrow ratio expressed by the formula (A).

The narrow ratio expressed by the formula (A) means a sum of alkylene oxide adducts having $n_{MAX}$ and alkylene oxide adducts having the number of moles of alkylene oxide added which is in the range of ±2 moles from the $n_{MAX}$, where $n_{MAX}$ is the number of moles of alkylene oxide added, which presents in the largest amount based on "% by mass" in the entire alkylene oxide adducts.

Here, the number of moles of alkylene oxide added is the total number of moles of EO and PO added. The adducts having the same number of moles of alkylene oxide added includes a plurality of alkylene oxide adducts having mutually different numbers of moles of EO added and different numbers of moles of PO added, but the same number of moles of alkylene oxide added on the whole.

The narrow ratio expressed by Formula (A) is 55% by mass or more, preferably 60% by mass or more, and more preferably 65% by mass or more. The higher narrow ratio is more preferable. However, in the case where a solid catalyst is used in the production, the production time is extended due to low filtration speed of the catalyst after the completion of the reaction, which increases a production cost. In the case where an alkali catalyst is used in the production, moreover, the production efficiency is lowered due to low yield resulted from the distillation, which increases a production cost. For these reasons, the upper limit of the narrow ratio is practically 95% by mass or less. When the narrow ratio is 55% by mass or more, the resulting surfactant composition has low foamability, and excellent defoamability and fluid stability.

The narrow ratio can be controlled by a production method of the fatty acid polyoxyalkylene alkyl ether expressed by the general formula (I).

The production method of the fatty acid polyoxyalkylene alkyl ether is suitably selected depending on the intended purpose without any restriction. Examples thereof include: a method in which a block addition polymerization of PO and EO are performed to fatty acid alkyl ester using a complex metal oxide catalyst (see JP-A No. 2000-144179); a method in which a block addition polymerization is performed on a lower alcohol, which is an equivalent of $R^2O$ using the aforementioned complex metal oxide catalyst (see JP-A 09-262456), and then the resultant is subjected to transesterification with suitable fatty acid ester, or the resultant is subjected to esterification with suitable fatty acid; and a method in which PO and EO added to the lower alcohol by a block addition polymerization using an alkali catalyst, followed by appropriately evaporating and removing unreacted lower alcohol or substances having low numbers of moles added to control the distribution of the numbers of moles added to have a desired narrow ratio, and then the resultant is subjected to transesterification with suitable fatty acid ester, or the resultant is subjected to esterification with suitable fatty acid.

When the block addition polymerization of PO and EO is performed to the fatty acid alkyl ester in the production of the fatty acid polyoxyalkylene alkyl ether, a catalyst for use is suitably selected without any restriction. For obtaining the fatty acid polyoxyalkylene alkyl ether having the desired narrow ratio without using other purification member such as evaporator, the catalyst for use is preferably a complex metal oxide catalyst, such as baked catalysts of hydrotalcite a surface of which is modified with metal hydroxide and/or metal alkoxide, and a complex metal oxide catalyst such as magnesium oxide to which metal ions (e.g. $Al^{3+}$, $Ga^{3+}$, $In^{3+}$, $Tl^{3+}$, $Co^{3+}$, $Sc^{3+}$, $La^{3+}$, and $Mn^{2+}$) whose surface is modification with alkali are added.

Specific examples of such catalyst include a catalyst which is obtained by surface modifying alumina-magnesia complex oxide with metal hydroxide or metal alkoxide, where the alumina-magnesia complex oxide is obtained by baking a corprecipitate of aluminum hydroxide and magnesium hydroxide, which is expressed by the general formula (2) below.

$$n\text{MgO}.\text{Al}_2\text{O}_3.m\text{H}_2\text{O} \tag{2}$$

In the general formula (2), n is not particularly limited, but preferably around 2.5, and m is not particularly limited.

The baking temperature of the coprecipitate is preferably 400° C. to 950° C., more preferably 500° C. to 750° C.

The metal hydroxide used for the modification is suitably selected depending on the intended purpose without any restriction, but it is preferably selected from hydroxides of alkali metals or alkali earth metals, more preferably selected from sodium hydroxide and potassium hydroxide.

The metal alkoxide is suitably selected depending on the intended purpose without any restriction, but is preferably selected from alkali metals, and alkali earth metals, more preferably selected from sodium alkoxide, and potassium alkoxide.

The production method of the modified catalyst is suitably selected depending on the intended purpose without any restriction. For example, there are methods such as a method in which baked alumina-magnesia complex oxide is modified with hydroxide or alkoxide of alkali metal or alkali earth metal in advance, and is used as a catalyst for a reaction, and a method in which a baked alumina-magnesia complex oxide is mixed with metal hydroxide or metal alkoxide in fatty acid alkyl ester, which is a raw material, in a reactor for alkoxylation to modify the catalyst in the fatty acid alkyl ester, and then a reaction with alkylene oxide is performed.

The former method is not particularly limited, but is preferably a method in which an aqueous solution or alcohol solution of metal hydroxide or metal alkoxide is sprayed onto the baked alumina-magnesia complex oxide, followed by drying or baking.

The latter method is not particularly limited, and the order for adding the baked alumina-magnesia complex oxide and the metal hydroxide or metal alkoxide to the raw material fatty acid alkyl ester is not particularly limited. For addition, it is preferred that the metal hydroxide or metal alkoxide is added in the form of a lower alcohol solution or aqueous solution for uniformly and more selectively partly modify the acid centers of the surface of the catalyst.

The amount of the metal hydroxide or metal alkoxide used for the modification of the baked alumina-magnesia complex oxide is not particularly limited, but is preferably 1% by mass to 20% by mass relative to the amount of the baked alumina-magnesia complex oxide.

In the case where the surface modification is not performed, the block addition reaction product having a desired narrow ratio may not be obtained. In such case, the desired narrow ratio of thereof may be obtained by the operation such as by evaporating substances having small numbers of moles of EO and PO added. Note that, in order to introduce PO at the terminal, it is necessary to perform a block addition polymerization in the order of PO and EO.

In the case the fatty acid polyoxyalkylene alkyl ether is produced by the method in which a block addition polymerization is performed on a lower alcohol, which is an equivalent of $R^2O$ using the aforementioned complex metal oxide catalyst, and then the resultant is subjected to transesterification with suitable fatty acid ester, or the resultant is subjected to esterification with suitable fatty acid, the complex metal oxide catalyst for use is not particularly limited, but can be selected from those listed above. Moreover, the complex metal oxide catalyst may be subjected to a surface modification, but in the case of the addition reaction to the lower alcohol, the desirable narrow ratio can be attained without performing the surface modification.

The addition reaction of ethylene oxide and propylene oxide using the solid catalyst can be performed in accordance with the common method. For example, the reaction temperature is not specifically limited, but generally is 80° C. to 230° C., preferably 120° C. to 190° C. The reaction pressure is, though it may be set depending on the reaction temperature, generally 0 MPa to 0.8 MPa, preferably 0.2 MPa to 0.5 MPa (gauge pressure).

The amount of the catalyst for use is changed depending on the molar ratio of alkylene oxide and fatty acid alkyl ester used in the reaction, but is generally 0.1% by mass to 20% by mass relative to the amount of the fatty acid alkyl ester.

In the case the fatty acid polyoxyalkylene alkyl ether is produced by the method in which a block addition polymerization is performed on a lower alcohol, which is an equivalent of $R^2O$ using the aforementioned complex metal oxide catalyst, and then the resultant is subjected to transesterification with suitable fatty acid ester, or the resultant is subjected to esterification with suitable fatty acid, a desirable narrow ratio cannot be obtained only by the addition reaction.

In order to obtain a block adduct having PO unit at the terminal as a final product in the present method, it is necessary to perform an addition reaction of PO first, followed by performing an addition reaction of EO.

In this case, as a method for obtaining a desirable narrow ratio, there is a method in which the unreacted raw material, adducts of low moles, and the like are removed from an intermediate product obtained from the addition reactions of PO and EO, by distillation. In the case where the unreacted raw material and the like are removed by distillation, the distillation is performed in the common method such as a vacuum distillation. It is preferred that the amount of the unreacted raw material be 2.5% by mass or less in the fatty acid polyoxyalkylene alkyl ether in view of permeability and fluid stability.

Moreover, the following methods are also preferable because the distribution of the number of moles of PO added and the distribution of the number of moles of EO added can be separately controlled, and a block adduct having a narrower distribution of the number of moles added can be easily obtained. Namely, they are a method in which unreacted substances and/or adducts of low moles are removed from an intermediate product 1 obtained from the addition reaction of PO, by distillation, and a method in which after the procedure of the former method, an addition reaction of EO is performed to attain a block adduct (an intermediate product 2), and adducts of low moles are again removed from the intermediate product 2 by distillation.

In this case, the narrow ratio of the intermediate product 1 calculated by Formula (A) is preferably 40% by mass or more in view of permeability and fluid stability, more preferably 50% by mass or more, and even more preferably 55% by mass or more. Moreover, the residual amount of the unreacted raw material alcohol is preferably 2.5% by mass or less in view of permeability and fluid stability, and more preferably 1.0% by mass or less in the total amount of the fatty acid polyoxyalkylene alkyl ether.

Such PO adduct having a high narrow ratio is not particularly limited. As such PO adduct, a commercially available raw material, which is obtained by performing an addition reaction of PO to a lower alcohol such as tripropylene glycol monomethyl ether (e.g. product name: methyl propylene triglycol (MFTG), manufactured by Nippon Nyukazai. Co., Ltd.), followed by superfractionation. Use of the PO adduct of a single number of moles added, which does not substantially have a distribution, by superfractionation or the like is preferable, because the resulting surfactant composition has particularly excellent permeability.

When the block adduct (the intermediate product 2) is obtained by performing an addition polymerization of EO to the intermediate product 1 having a narrow distribution of the numbers of moles added, the residual intermediate product 1 to which EO has not been added or adducts of low moles of EO added are removed from the intermediate product 2 by distillation or the like so that the resultant has a sharp distribution of numbers of moles of EO added. As a result, the resulting surface composition has excellent foamability and defoamability. Moreover, when the resulting surface composition is formulated by mixing with a solvent such as water or lower alcohol, such formulation has excellent low temperature stability, preventing uniformity, precipitation, or solidification. The removal of the adduct of low moles from the intermediate product 2 by distillation can be performed by a common method such as a vacuum distillation. Moreover, those obtained by the aforementioned production method may be produced and used singly or in an appropriate combination.

Examples of the production method of the fatty acid polyoxyalkylene alkyl ether include a method in which a block addition polymerization is performed with lower alcohol, which is an equivalence of $R^2O$ using the complex metal oxide catalyst in the same manner (see JP-A No. 09-262456) followed by transesterification with suitable fatty acid ester or exterification with suitable fatty acid, and a method in which PO and EO are added and polymerized to the lower alcohol in the form of a block polymer using an alkali catalyst, and then unreacted lower alcohol or adduct components of low moles are removed by distillation to control a distribution of numbers of moles added to thereby have a desirable narrow ratio, followed by transesterification with suitable fatty acid ester or exterification with suitable fatty acid. Here, the catalyst for used in the transesterification with suitable fatty acid ester or exterification with suitable fatty acid is suitably selected depending on the intended purpose without any restriction. Examples thereof include basic catalysts such as lithium hydroxide, cesium hydroxide, sodium hydroxide, potassium hydroxide, magnesium hydroxide, barium hydroxide, calcium hydroxide, sodium carbonate, potassium carbonate, sodium hydrogen carbonate, lithium chloride, sodium formate, and sodium methoxide. Examples of acid catalysts include sulfuric acid, zirconium sulfonate, p-toluene sulfonic acid (p-TS), benzene sulfonic acid (BS), and 2,4-dimethyl-benzene sulfonic acid (2,4-DMBS). Examples of inorganic oxide catalysts include $ZrO_2$, $TiO_2$, $SiO_2$, $PO_4$, $Al_2O_3$, and ZnO.

The catalyst used for room temperature transesterification is suitably elected depending on the intended purpose without any restriction. Examples of such catalyst include a tin compound, such as dialkyl tin chloride, dialkyl tin oxide, fluoro-alkyl tin, and aminopropyl tin.

Other examples thereof include titanium compounds such as tetraisopropyl titanate, tetra-n-butyl titanate, tetraethanol amine titanate, and tetrastearyl titanate. In addition, examples thereof include, other than those listed above, samarium iodide, and N-heterocyclic carbine. Further examples thereof include lanthanum(III)triisopropoxide([La(Oi.Pr)$_3$]), lanthanum(III)tristrifluoromethylsulfonate ([La(OTf)$_3$]), lanthanumtrisacetylacetonate, lead compounds such as lead acetate and lead naphthenate, litharge, calcium naphthenate, and enzyme.

The surfactant composition for agricultural chemicals is used as a raw material of an agricultural pesticide, and thus it is not desirable that titanium or tin is left therein. Therefore, it is preferred that the surfactant composition be subjected to an adsorption treatment or filtration purification. Particularly preferable embodiment in view of the environment is such that sodium hydroxide, sodium hydrogen carbonate, or sodium methoxide is used as a catalyst for transesterification or esterification, and then an adsorption treatment or filtration purification is performed.

When the transesterification is performed with fatty acid ester such as fatty acid methyl ester in the course of the production of the fatty acid polyoxyalkylene alkyl ether, the residual amount of the fatty acid ester in the resulting fatty acid polyoxyalkylene alkyl ether is preferably 3.0% by mass or less, more preferably 2.0% by mass or less in view of the fluid stability and permeability.

The surfactant composition of the agricultural pesticide is suitably used as a spreading agent of an agricultural pesticide containing an agricultural pesticide active ingredient, is suitably formulated and used in a fluid agricultural pesticide formulation as a dispersing agent, or solubilizing agent of an agricultural pesticide active ingredient and the like, or is suitably used together with a fluid agricultural pesticide as a spreading agent for agricultural chemicals.

In the case where the surfactant composition for agricultural chemicals of the present invention is used as a spreading agent for agricultural chemicals, for example, it is generally mixed in a chemical solution of an agricultural pesticide and is used at the time when the agricultural pesticide is sprayed. The concentration thereof for use is generally about 30 ppm to about 5,000 ppm in water, and is suitably adjusted depending on an agricultural pesticide for use, or whether or not a targeted plant is easily wet.

In the case where the surfactant composition for agricultural chemicals is used as a spreading agent for agricultural chemicals, it is preferred that the surfactant be mixed with water and a solvent, and used as a mixed solution, because the fatty acid polyoxyalkylene alkyl ether is not easily dissolved in water.

Examples of the solvent include lower alcohol and glycols, since these can be easily dissolve the fatty acid polyoxyalkylene alkyl ether therein, and are easily mixed with water.

In the present specification, the term "lower alcohol" means C1-4 alcohol.

The lower alcohol is suitably selected depending on the intended purpose without any restriction, and examples thereof include methanol, ethanol, isopropyl alcohol, n-propyl alcohol, isobutyl alcohol, and n-butyl alcohol.

The glycols are suitably selected depending on the intended purpose without any restriction, and examples thereof include ethylene glycol, and propylene glycol. Moreover, acetone, propylene carbonate, N-methylpyrrolidone, γ-butyrolactone, or the like may also be used as the solvent. Concerning that it is released to the environment as a spreading agent for agricultural chemicals, ethanol, isopropyl alcohol, and isobutyl alcohol are preferable. In view of a high flash point for increasing safety, isopropyl alcohol and isobutyl alcohol are suitable.

In the case where the surfactant composition for agricultural chemicals is used as a spreading agent for agricultural chemicals, a proportion of the fatty acid polyoxyalkylene alkyl ether serving as a surfactant in the surfactant composition for agricultural chemicals is 10% by mass to 60% by mass, preferably 20% by mass to 40% by mass, a proportion of water therein is 10% by mass to 70% by mass, preferably 20% by mass to 60% by mass, and a proportion of the lower alcohol therein is 10% by mass to 70% by mass, preferably 20% by mass to 50% by mass. Instead of the lower alcohol, a solvent formed of the glycols or a mixed solution of the lower alcohol and the glycols can be used at the same proportion.

In the case where the surfactant composition for agricultural chemicals is used as a spreading agent for agricultural chemicals, a specific example of a formulation of the surfactant composition for agricultural chemicals is consisted of 30% by mass of a surfactant of the fatty acid polyoxyalkylene alkyl ether; 30% by mass of water; and 40% by mass of isopropyl alcohol (i.e. a surfactant of the fatty acid polyoxyalkylene alkyl ether/water/isopropyl alcohol=30% by mass/30% by mass/40% by mass), which is preferable in view of its excellent low temperature stability.

In addition to the above, the surfactant composition for agricultural chemicals serving as a spreading agent for agricultural chemicals can contain a sticking agent such as carboxymethylcellulose, Arabian gum, and casein, and a dispersing agent such as a naphthalenesulfonic acid-formaldehyde condensate, and lignin sulfonate, if necessary.

The surfactant composition for agricultural chemicals can be used, as an activator for agricultural chemicals, for a functional spreading agent (adjuvant), water dispersible agent, emulsifier, and dispersing and dissolving agent. Moreover, it can be used as a surfactant for agricultural chemicals such as a bactericide, insecticide, acaricide, weedkiller, and plant growth regulator.

In the case where the surfactant composition for agricultural chemicals is used as the dispersing and dissolving agent for a preparation of an agricultural pesticide, an amount of the surfactant composition for agricultural chemicals for use as a surfactant is about 5% by mass to about 50% by mass.

The present invention can provide a surfactant composition, which has low foamability, excellent defoamability, and excellent low temperature stability, prevents separation (heterogeneity), precipitation, and solidification, when it is formulated as a preparation where the surfactant composition is mixed with a solvent such as water, lower alcohol, and the like as mentioned above, and which is suitably applied and easily handled as a spreading agent for agricultural chemicals, or a dispersing and dissolving agent for a preparation of an agricultural pesticide.

Since this surfactant composition is an excellently environmentally safe surfactant composition, which can be used in the field of agricultural pesticides, the surfactant can also be used as a surfactant in the fields of engineering works, energy industries, in which the surfactant will be released in the environment.

EXAMPLES

The present invention will be more specifically explained through Examples thereof, hereinafter. However, these Examples shall not be construed as to limit a scope of the present invention. The evaluation methods and analysis methods used in Examples are shown below.
(1) Evaluation Method
(i) Foaming power and Defoamability To a 1,000-ml, graduated cylinder, 100 mL of a test solution having an active ingredient concentration of 1,000 ppm was added. To this solution, nitrogen gas was introduced from the bottom of the cylinder at the rate of 1,000 mL/min. for 3 minutes using a glass ball filter (Filter Particle No. 4 (5 μm to 10 μm in size), manufactured by Kinoshita Rika Kogyo Co., Ltd.). Just after the completion of the introduction of the nitrogen gas, a foam height was measured, and was determined as a foaming power. In addition, the defoamability was determined based on the foam height just after the completion of the introduction, and the height thereof 5 minutes after the completion of the introduction, using the following formula.

Defoamability(%)=(foam height just after the completion−foam height 5 minutes later)/foam height just after the completion×100

The foaming power and defoamability were evaluated based on the following criteria.

<Evaluation Criteria of Foaming Power (Foam Height)>
A: 0 mm or higher but lower than 90 mm
B: 90 mm or higher, but lower than 120 mm
C: 120 mm or higher <Evaluation Criteria of Defoamability>
A: 70% or more
B: 40% or more but less than 70%
C: less than 40%

(ii) Permeability (Wettability)

A test was carried out in accordance with the Draves method. A piece of wool knit cloth was cut out in the size of 20 cm in length and 3 cm in width to prepare a sample cloth. A wire tool was provided so that a wire anchor part of the tool would stay on the bottom of a 1,000-mL graduated cylinder, and the wire anchor part and a snake pin hook (about 0.1 g) were connected with a nylon thread (about 3 cm). A test solution was prepared by diluting each surfactant sample to 30 ppm with hard water having a hardness index of 3, and was added to the 1,000-mL graduated cylinder. One side of the test cloth was hanged on the snake pin hook, and the wire tool was placed in the 1,000-mL graduated cylinder in which the test solution was provided so that the wire anchor portion was sank and located on the bottom of the cylinder and the test cloth was floated in the test solution. The time from when the snake pin hook was placed in the test solution to when the snake pin hook started to sink (when the thread between the hook and the anchor lost tension) was measured. The shorter the time is, more preferable the permeability is. The time shorter than 30 second was determined as acceptable, and the time equal to or longer than 30 seconds was determined as unacceptable.

(Iii) Fluid Stability Test

A solution was prepared with 30 parts by mass of a surfactant sample, 30 parts by mass of ion-exchanged water, and 40 parts by mass of isopropyl alcohol, and the solution was stirred until it became homogeneous. Then, the resulting solution was placed in a sample bottle, and the sample bottle was sealed, and placed in a constant temperature oven the temperature of which was set to −5° C. for 72 hours. After this storage period, the solution which kept its homogeneous state at −5° C. was determined as A, the solution which had precipitates or caused fluid separation, but recovered its homogeneous state when it was heated to 20° C. was determined B, and the solution which did not recover the precipitation or fluid separation was determined as C.

(iv) Solubility

An aqueous solution of each surfactant sample was prepared at the concentration of 1,000 ppm as a sample solution. To 4 mL of this sample solution, an oil soluble coloring agent Yellow OB was added in an amount of 40 mg as an insoluble substance, and the mixture was agitated at room temperature for 24 hours. Thereafter, the resulting solution was filtered through a pretreatment filter (Chromatodisk, manufactured by GL Sciences Inc., 13N, non-water system, nonstelarized) having an opening size of 0.45 μm, followed by adding an equal amount of ethanol. An absorption of the resulting solution was measured at 450 nm. As the dissolved amount, the amount which was 30 ppm or more was determined as acceptable, and the amount less than 30 ppm was determined as unacceptable.

(v) Biodegradability

A test was performed with reference to a degradation test of a chemical substance by microbes or the like in accordance with Act on the Evaluation of Chemical Substances and Regulation of their manufacture, etc. (CSCL). Specifically, activated sludge was added in an amount of 30 ppm (solid contents) was added as a seeding source to a test solution having a sample concentration of 100 ppm, and a biochemical oxygen demand (BOD) and the total oxygen demand (TOD) were measured over time. The results of the biodegradation degree, i.e. BOD/TOD (%), were evaluated based on the following criteria.

A: The biodegradation degree reached 60% within 28 days.
B: It took 29 days or longer for the biodegration degree to reach 60%, or the sample was only decomposed at a certain amount but not more than that amount.

(vi) Fish Toxicity

A fish toxicity value, a median tolerance limit (TLm)(48 hours), was measured on Japanese variety of cyprinodonts with reference to "71. Acute toxycity test for fish", defined in Testing methos for industrial wastewater JIS K 0102, namely the median lethal concentration (ppm) was measured after 48 hours. The result which was 100 ppm or higher was defined as acceptable, and the result which was lower than 100 ppm was defined as unacceptable.

(vii) Phytotoxicity

The sample was sprayed to cabbage and garden pea as an active ingredient (5,000 ppm) of a spreading agent, and a rate of phytotoxicity occurred was determined 5 days later. The result of the rate of the phytotoxicity which was less than 30% was determined as acceptable, and the result of the rate thereof which was 30% or more was determined as unacceptable.

(3) Analysis Method

The analysis method used is described hereinafter. The average numbers of moles of EO, and PO added were calculated from the balance of the masses of the charged raw materials and alkylene oxide. Note that, in the case where the distillation was performed after the addition reaction of EO and PO, the average number of moles added was determined by $^1$H-NMR described in (i) below.

(i) Calcularation Method of Average Number of Moles Added

The obtained compound (30 mg) was dissolved in 4 mL of deuterochloroform, and the solution was then measured by $^1$H-NMR (300 MHz, FT NMR SYSTEM JNM-LA300, manufactured by JEOL Ltd.). The chemical shift of the deuterochloroform was calculated, using 7.30 ppm as a standard, from the integral value ratio of chemical shift of each peak, 0.87 ppm (terminal methyl of fatty acid), 1.13 ppm to 1.15 ppm (side chain methyl of PO), 3.32 ppm to 3.66 ppm (methine and methylene of PO), and 3.52 ppm to 3.71 ppm (methylene of EO).

(ii) Measurement of Distribution of Numbers of Moles EO and PO Added, and Calculation Method of Narrow Ratio The distributions of numbers of moles of EO and PO added of the final product and intermediate product were measured in the following manner.

Condition of Device: gas chromatograph: HP-6890 Mass Selective Detector(GC-MS),
Detector: FID
Column: UltraALLOYPY-1, 0.25 mm in diameter, 30 m in length, film thickness of 0.25 μm
Condition of Analysis Injection: 380° C., Detector: 380° C.
Initial: 50° C. 360° C. (20 min), temperature increasing rate: 10° C./min, carrier gas:
He
Split ratio: 50/1

The sample (0.5 g) was dissolved in 10 g of acetone, 1 μL of the obtained solution was introduced to the device, and a concentration (%) per mole of EO (PO) added was measured. The total proportion of the maximum peak of the obtained chromatogram and adducts in the range of ±2 moles of the maximum peak (the total of adducts in range of 5 moles) was determined as a narrow ratio.

$$\text{Narrow ratio} = \Sigma_{i=n_{MAX-2}}^{i=n_{MAX+2}} Y_i \quad (A)$$

(Iii) Determination of Amount of Unreacted Fatty Acid Methyl Ester or Unreacted Methanol Contained in Intermediate Product 1 or 2

(1) For Unreacted Fatty Acid Methyl Ester

As internal standard, 0.06 g of methayl laurate and 2 g of a sample were prepared and dissolved in 4 g of acetone, and the obtained solution (2 µL) was introduced to a device. An analytical curve was formed from the peak area of the internal standard, and the peak area obtained when the concentration of methyl laurate was changed, and an amount of an unreacted component contained the sample was determined.

(2) For Unreacted Methanol

A sample (1 µL) was introduced to a device without diluting with a solvent, and an amount of unreacted methanol was calculated from the area % of the obtained chromatogram.

<Conditions for Device>

Gas chromatograph: Shimadzu GC-14A, detecting element: FID, Column: made of glass 3 mm in diameter×1 m, fillers: 2% silicon OV-1 (60/80 mesh)

—Universal Conditions—

Injection: 320° C., Detector: 320° C., $N_2$: 50 mL/min, $H_2$: 0.75 kg/cm$^2$, Air: 0.5 kg/cm$^2$ —For Unreacted Methyl Ester—

Initial: 100° C.→230° C. (increasing rate of temperature: 10° C./min) 320° C. (increasing rate of temperature: 30° C./min, duration for maintaining the temperature: 22 min —For Unreacted Methanol—

Initial: 50° C.→320° C. (maintaining for 20 min), increasing rate of temperature:10° C./min Example 1

An alumina-magnesia complex oxide (Kyowado 300, manufactured by Kyowa Chemical Industry Co., Ltd.) expressed by the chemical formula 2.5MgO.Al$_2$O$_3$.nH$_2$O was baked at 750° C. for 3 hours under nitrogen gas streams to thereby obtain a baked alumina-magnesia complex oxide (Al/Mg molar ratio=0.44/0.56) catalyst. Into a 4-L autoclave, 1,073 g of methyl oleate (fatty acid methyl ester derived from C18 fractions derived from palm oil, product name: PAS-TELL M182, manufacturer: Lion Corporation, iodine value: 91), 5 g of the obtained catalyst, and 0.58 g of 40% KOH as a modifying agent for the catalyst were added, and the inner atmosphere of the autoclave was replaced with nitrogen gas twice.

Thereafter, the temperature was increased to 180° C., the pressure inside the reaction vessel was returned to normal pressure by nitrogen, and then 628 g of PO (3 moles relative to 1 mole of methyl oleate) was gradually introduced to the vessel. The pressure just after the completion of the introduction of PO was 0.48 MPa, and was reduced as the reaction progressed. The PO addition reaction was continued until the pressure became constant at 0.22 MPa in 2 hours. A portion of the obtained intermediate product 1A was sampled, and then analyzed by gas chromatography. As a result, the sample contained 12.8% by mass of unreacted fatty acid methyl ester.

Then, after the nitrogen purge was performed and the temperature was increased in the aforementioned manners, 794 g of EO (5 moles relative to 1 mole of methyl oleate) was gradually introduced to the vessel. The pressure just after the completion of the introduction of EO was 0.5 MPa, and was reduced as the reaction progressed. The EO addition reaction was continued until the pressure became constant at 0.24 MPa in 0.5 hours time. The obtained reaction product was filtered using diatom earth to thereby obtain a final product. The compound 1A obtained by a block addition reaction of PO and EO contained 1.1% by mass of unreacted fatty acid methyl ester. Results of measurements and evaluation were shown in Tables 1 and 2.

Example 2

A compound 1B was obtained by a block addition reaction of PO and EO in the same manner as in Example 1, provided that the amount of PO added was changed to 565 g (2.7 moles relative to 1 mole of methyl oleate), and the obtained intermediate product 1B was subjected to vacuum distillation by reducing the pressure to 10 Torr or lower, while increasing the temperature stepwise from 175° C. to 200° C. stepwise, so as to remove unreacted methyl ester contained in the intermediate product 1B. The intermediate product 1B contained 0.8% by mass of unreacted fatty acid methyl ester. The compound 1B obtained by further subjecting to an addition reaction of EO contained 0.3% by mass of unreacted fatty acid methyl ester. The results of measurements and evaluation are shown in Tables 1 and 2.

Example 3

A compound 1C was obtained by performed a block addition reaction of PO and EO in the same manner as in Example 2, provided that 40% KOH was not added as the modifying agent for the catalyst. The intermediate product 1C after the vacuum distillation contained 1.8% by mass of fatty acid methyl ester. The compound 1C obtained by further subjecting to an addition reaction of EO contained 1.6% by mass of unreacted fatty acid methyl ester. The results of measurements and evaluation are shown in Tables 1 and 2.

Comparative Example 1

A final product was obtained in the same manner as in Example 1, provided that a mixture of 794 g of EO (5 moles relative to 1 mole of methyl oleate) and 628 g of PO (3 moles relative to 1 mole of methyl oleate) was gradually introduced to the vessel, and then a random addition reaction of EO and PO was performed. The pressure in the vessel was 0.48 MPa just after the completion of the mixture, but was reduced as the random addition reaction of EO and PO progressed. The random addition reaction was continued until the innter pressure became constant at 0.24 MPa in 2 hours time. The compound 1D obtained by the random addition reaction of EO and PO contained L2% by mass of unreacted fatty acid methyl ester. The results of measurements and evaluation are shown in Tables 1 and 2.

Comparative Example 2

A final product was obtained in the same manner as in Example 1, provided that the order of the block addition was changed from "PO first and then EO" to "EO first and then PO". The compound 1E obtained by the block addition reaction of EO and PO contained 1.1% by mass of unreacted fatty acid methyl ester. The results of measurements and evaluation are shown in Tables 1 and 2.

Comparative Example 3

A final product was obtained in the same manner as in Example 1, provided that 40% KOH was not added as the modifying agent for the catalyst. The compound 1F obtained by the block addition reaction of PO and EO contained 4.9% by mass of unreacted fatty acid methyl ester. The results of measurements and evaluation are shown in Tables 1 and 2.

Example 4

Into a 4-L autoclave, 387 g of methanol (manufactured by Junsei Chemical Co., Ltd.), and 1 g of NaOH as a catalyst were added, and the inner atmosphere of the autoclave was replaced with nitrogen gas twice. Thereafter, the temperature was increased to 90° C., and then 1,405 g of PO (2.0 moles relative to 1 mole of methanol) was gradually introduced to the vessel to proceed an addition reaction.

After the completion of the reaction, the temperature was increased stepwise from 75° C. to 100° C. under normal pressure, and distillation was performed until the methanol residue became 1% or lower, to thereby obtain an intermediate product 2A1. The average number of moles of PO added of the intermediate product 2A1 was 2.4 moles. Thereafter, to 857 g of the intermediate product 2A1, 881 g of EO (4 moles relative to 1 mole of the intermediate product 2A1) was introduced, and an addition reaction was performed. After the addition reaction was completed, distillation was again performed by reducing the pressure to 10 Torr, while increasing the temperature stepwise from 175° C. to 220° C. Into a reaction vessel fitted with a stirring blade, 853 g of the obtained intermediate product 2A2, 614 g of methyl oleate (PASTELL M182, iodine value: 91) (1.03 moles relative to 1 mole of the intermediate product 2A2), and 7.3 g of sodium hydrogen carbonate were added, and the temperature was increased from 60° C. to 210° C. under stirring while reducing the pressure stepwise from normal pressure to 10 Torr to thereby perform transesterification. The compound 2A obtained by the reaction contained 1.6% by mass of unreacted fatty acid methyl ester. The results of measurements and evaluation are shown in Tables 1 and 2.

Example 5

An addition reaction of PO was performed in the same manner as in Example 4, provided that the amount of PO introduced was changed to 2,108 g (3 moles relative to 1 mole of methanol). After the completion of the reaction, distillation was performed under normal pressure while increasing the temperature stepwise from 75° C. to 130° C., until the proportion of the methanol residue and methanol-1PO product was 1% or less. Then, vacuum distillation was further performed by increasing the temperature stepwise from 175° C. to 220° C. while reducing the pressure stepwise to 5 Torr, and then the distillate was collected so as to give an intermediate product 2B1 from which the portion of high boiling substances had been removed. The average number of moles of PO added of the intermediate product 2B1 was 3 moles.

To the intermediate product 2B1, an addition reaction of EO was performed in the same manner as in Example 4 to thereby obtain an intermediate product 2B2. then, to the intermediate product 2B2, transesterification was performed in the same manner as in Example 4, to thereby obtain a compound 2B. The obtained compound 2B contained L6% by mass of unreacted fatty acid methyl ester. The results of measurements and evaluation are shown in Tables 1 and 2.

Example 6

A block addition reaction of PO and EO was performed in the same manner as in Example 4 to thereby obtain an intermediate product 2C2, provided that an addition reaction of PO was performed in the manner that the amount of PO introduced was changed to 1,686 g (2.4 moles related to 1 mole of methanol) and the distillation was not performed after the addition reaction of PO, and to the intermediate product 2C2 transesterification reaction was performed in the same manner as in Example 4 to thereby obtain a compound 2C.

The intermediate product 2C1 contained L9% by mass of unreacted methanol, and the obtained compound 2C contained 1.7% by mass of unreacted fatty acid methyl ester. The results of measurements and evaluation are shown in Tables 1 and 2.

Comparative Example 4

A compound 2D was obtained in the same manner as in Example 6, provided that the addition reaction of PO was performed in the manner that the amount of PO introduced was changed to 2,108 g (3 moles relative to 1 mole of methanol), the addition reaction of EO was performed in the manner that the amount of EO introduced was changed to 1,289 g (5 moles relative to 1 mole of methanol), and vacuum distillation was not performed after the addition reaction of EO. The intermediate product 2D1 contained 10.3% by mass of unreacted methanol, and the obtained compound 2D contained 1.6% by mass of unreacted fatty acid methyl ester. The results of measurements and evaluation are shown in Tables 1 and 2.

Note that, the sample used for each example was also evaluated in terms of biodegradation ability, fish toxicity, and phytotoxicity, and as a result, it was confirmed that all the samples had excellent biodegradation ability (evaluation: A), and were highly safe in the environment, which passed the acceptable levels of the results of the tests for fish toxicity and phytotoxicity.

TABLE 1

| | Sample No. | Starting material | Catalyst | EO/PO addition form | Average number of moles added EO | Average number of moles added PO | Position of PO | Narrow ratio (mass %) |
|---|---|---|---|---|---|---|---|---|
| Ex. 1 | 1A | Fatty acid methyl ester | Modified solid | Block | 5 | 3 | Terminal | 68 |
| Ex. 2 | 1B | Fatty acid methyl ester | Modified solid | Block | 5 | 3 | Terminal | 76 |

TABLE 1-continued

| Sample No. | Starting material | Catalyst | EO/PO addition form | Average number of moles added EO | PO | Position of PO | Narrow ratio (mass %) |
|---|---|---|---|---|---|---|---|
| Ex. 3 | 1C | Fatty acid methyl ester | Non-modified solid | Block | 5 | 3 | Terminal | 60 |
| Comp. Ex. 1 | 1D | Fatty acid methyl ester | Modified solid | Random | 5 | 3 | Inner portion | 69 |
| Comp. Ex. 2 | 1E | Fatty acid methyl ester | Modified solid | Block | 5 | 3 | Inner portion | 66 |
| Comp. Ex. 3 | 1F | Fatty acid methyl ester | Non-modified solid | Block | 5 | 3 | Terminal | 43 |
| Ex. 4 | 2A | Methanol | NaOH | Block | 5 | 3 | Terminal | 65 |
| Ex. 5 | 2B | Methanol | NaOH | Block | 5 | 3 | Terminal | 71 |
| Ex. 6 | 2C | Methanol | NaOH | Block | 5 | 3 | Terminal | 61 |
| Comp. Ex. 4 | 2D | Methanol | NaOH | Block | 5 | 3 | Terminal | 48 |

TABLE 2

| Sample No. | Foaming power Foam height (mm) | Evaluation | Defoamability Value (%) | Evaluation | Permeability (sec.) | Fluid stability |
|---|---|---|---|---|---|---|
| Ex. 1 | 1A | 62 | A | 79 | A | 18 | B |
| Ex. 2 | 1B | 49 | A | 85 | A | 14 | A |
| Ex., 3 | 1C | 85 | A | 71 | A | 28 | B |
| Comp. Ex. 1 | 1D | 113 | B | 51 | B | 45 | C |
| Comp. Ex. 2 | 1E | 176 | C | 36 | C | 83 | C |
| Comp Ex. 3 | 1F | 97 | B | 64 | B | 37 | C |
| Ex. 4 | 2A | 73 | A | 75 | A | 22 | B |
| Ex 5 | 2B | 55 | A | 82 | A | 16 | A |
| Ex. 6 | 2C | 89 | A | 70 | A | 29 | B |
| Comp. Ex. 4 | 2D | 143 | C | 45 | C | 57 | C |

What is claimed is:

1. A method for preparing a surfactant composition for agricultural chemicals, comprising:
  1) adding propylene oxide (PO) to a lower alcohol by a block addition polymerization to form an intermediate product 1,
    removing, by distillation, unreacted lower alcohol or substances having low numbers of moles added, to form intermediate product 2,
    adding ethylene oxide (EO) to the intermediate product 2 by a block addition polymerization to form an intermediate product 3,
    removing, by distillation, unreacted lower alcohol or substances having low numbers of moles added to form an intermediate product 4, and
    transesterifying the intermediate product 4 with fatty acid ester or esterifying the intermediate product 4 with fatty acid to obtain the surfactant composition for agricultural chemicals,
    wherein the procedure is performed in recited order,
    wherein the surfactant composition for agricultural chemicals, comprising: fatty acid polyoxyalkylene alkyl ether expressed by the following general formula (I), $$R^1CO(EO)_m(PO)_nOR^2 \quad (I)$$

where $R^1CO$ is a C14-22 saturated or unsaturated fatty acid residue; $R^2$ is a C1-3 alkyl group; m and n each express an average number of moles added, where m is an integer of 2 to 10, and n is an integer of 1 to 4; and EO expresses a structural unit of ethylene oxide, and PO expresses a structural unit of propylene oxide, where a form of additions of EO and PO is a block polymer,
    wherein the fatty acid polyoxyalkylene alkyl ether has a narrow ratio of 55% by mass or more, where the narrow ratio is expressed by the following formula (A):

$$\text{Narrow ratio}=\Sigma_{i=n_{MAX}-2}^{i=n_{MAX}+2} Y_i \quad (A)$$

where i is the number of moles of alkylene oxide added (the total number of moles of EO and PO which are added), $n_{MAX}$ is the value of i of the fatty acid polyoxyalkylene alkyl ether whose number of moles of alkylene oxide added presents in the largest amount on mass basis among all the fatty acid polyoxyalkylene alkyl ether expressed by the general formula (I), and Yi is a proportion (% by mass) of the fatty acid polyoxyalkylene alkyl ether whose number of moles of alkylene oxide added is i in the entire fatty acid polyoxyalkylene alkyl ether.

* * * * *